United States Patent [19]

LaMarre et al.

[11] Patent Number: 4,616,037
[45] Date of Patent: Oct. 7, 1986

[54] SYNERGISTIC BIOCIDE OF 1,5-PENTANEDIAL AND METHYLENE BIS THIOCYANATE

[75] Inventors: Thomas M. LaMarre, Aurora; Cynthia H. Martin, Joliet, both of Ill.

[73] Assignee: Nalco Chemical Company, Oak Brook, Ill.

[21] Appl. No.: 759,781

[22] Filed: Jul. 29, 1985

[51] Int. Cl.$^4$ .................. A01N 47/40; A01N 47/46; A01N 47/48; A01N 35/00
[52] U.S. Cl. ................................ 514/515; 514/516; 514/705
[58] Field of Search ................ 514/515, 516, 705

[56] References Cited

U.S. PATENT DOCUMENTS

| | | | |
|---|---|---|---|
| 2,801,216 | 7/1957 | Yoder et al. | 514/705 |
| 3,252,855 | 5/1966 | Wehner | 167/22 |
| 3,300,375 | 1/1967 | Wehner | 167/22 |
| 3,664,821 | 5/1972 | Shema et al. | 71/67 |
| 3,674,457 | 7/1972 | Wolfson | 514/515 |
| 3,928,198 | 12/1975 | Brink et al. | 71/67 |
| 4,285,765 | 8/1981 | Pera et al. | 71/67 |
| 4,479,961 | 10/1984 | Martin | 514/367 |

OTHER PUBLICATIONS

Kull, S. C., Eisman, P. C., Sylwestrowicz, H. D., Mayer, R. L., *Applied Microbiology*, vol. 9, pp. 538–541, (1936).

Primary Examiner—Albert T. Meyers
Assistant Examiner—John M. Kilcoyne
Attorney, Agent, or Firm—John G. Premo; Donald G. Epple

[57] ABSTRACT

A superior industrial biocide for treating industrial process waters is afforded in the combination of 1,5-pentanedial and methylene bis thiocyanate.

1 Claim, No Drawings

SYNERGISTIC BIOCIDE OF 1,5-PENTANEDIAL AND METHYLENE BIS THIOCYANATE

INTRODUCTION

A well known microbiocide used to treat a variety of industrial process waters is methylene bis thiocyanate. The use of this material for treating industrial process water which contain a variety of anaerobic bacteria and its use in treating aerobic bacteria such as sulfate reducing bacteria is disclosed in U.S. Pat. Nos. 3,252,855 and 3,300,375, the disclosure of which is incorporated herein by reference.

The present invention relates to the use of methylene bis thiocyanate in combination with the toxicant, 1,5-pentanedial to provide a superior synergistic biocidal composition.

THE INVENTION

A synergistic biocidal composition useful in treating industrial process waters to prevent the growth of micro-organisms which comprises from 5-95% by weight of methylene bis thiocyanate and from 95-5% by weight of 1,5-pentanedial. The compositions of the invention are effective when used at a dosage of a few parts per million.

The synergistic blends described above may be used to treat a wide variety of aerobic and anaerobic bacteria. While the invention is described primarily with respect to the control of bacteria, it is understood that the term, "bacteria," as used herein also includes fungi and other micro-organisms.

The mechanisms by which chemical agents exert antimicrobial activity depend upon the effective contact between the chemical and microorganism and involve disruptive interaction with a biochemical or physical component of the organism, which component is essential to its structure or metabolism. The targets may be an enzyme, or enzymes, the cell membrane, intracellular systems, the cytoplasm, or combination of these, and the nature of the action is dependent on the organism, on the antimicrobial agent, and on the environment in which the interaction occurs. 1,5-pentanedial, for example, often acts through the alkylation of amino and sulfhydryl groups of proteins. Methylene bisthiocyanate blocks the transfer of electrons by reacting with the trivalent iron which in normal cellular respiration accepts electrons from the primary cytochrome dehydrohygenase; the ferric iron is thus deactivated, causing the immediate death of the cell. Methylene bisthiocyanate is a powerful toxicant to bacteria, algae and fungi; 1,5-pentanedial is also a toxicant to these microorganisms and is sporicidal as well.

The present invention relates to the use of methylene bisthiocyanate in combination with the toxicant, 1,5-pentanedial, to provide superior antimicrobial activity through a synergy in which the disruptive interaction on the organism by the two toxicants together is greater than the sum of both toxicants taken alone. The synergy does not arise from an expected additivity of the components or from a predictable improvement in activity. In all cases, the synergism depends largely on the interactions of the antimicrobial agents with the organism, the cellular processes of this latter being so complex in these interactions as to render such synergism an unpredictable, and indeed rare, phenomenon.

The synergism of these two components is demonstrated by adding 1,5-pentanedial (PD) and methylene bis-thiocyanate (MBT) in varying ratios over a range of concentrations to liquid nutrient medium. In this study of the control of bacterial growth, the nutrient medium was tryptone glucose extract agar. The concentrations of the above toxicants were added to aliquots of medium at a temperature of 50° C. Once treated, the medium was poured into sterile Petri dishes and allowed to solidify. Each test plate was inoculated with a bacterial suspension containing 0.1 ml of a nutrient broth culture of *Psuedomonas aeruginosa*. After an incubation at 37° C. for over forth-eight hours, the lowest concentration of each toxicant or of each ratio of the combined toxicants that prevented growth on the agar was taken as the end point.

The end points of each of the ratios tested were then compared with end points of the concentrations of the pure toxicants. Synergism was determined according to the industrially-accepted method described by S. C. Kull, P. C. Eisman, H. D. Sylwestrowicz, and R. L. Mayer in *Applied Microbiology*, Vol 9, pages 538-541, (1936), which is herein included as reference.

As regards the Kull et al. document, the data here presented can be described as follows:

$Q_A$=the ppm of actives of PD alone which produced an end point $Q_a$=the ppm of actives of PD, in combination, which produced an endpoint.

$Q_B$=the ppm of actives of MBT alone which produced an endpoint $Q_b$=the ppm of actives of MBT, in combination, which produced an endpoint $$\text{if } \frac{Q_a}{Q_A} + \frac{Q_b}{Q_B} < 1 \text{ indicates synergy}$$

$$> 1 \text{ indicates antagonism}$$

$$= 1 \text{ indicates additivity}$$

Ratios of PD/MBT: 100/0, 0/100, 90/10, 10/90, 75/25, 25/75, 50/50.

Concentrations tested for each ratio in terms of parts per million of actives: 0.3, 0.6, 1.0, 1.5, 3.0, 5.0, 7.5, 10, 20, 30, 40, 50, 60, 70, 80, 90, 100, 200, 300, 400, 500, 600, 700, 800, 900, 1000.

TABLE I

SYNERGISM STUDY FOR COMBINATION BIOCIDES AGAINST BACTERIA

Growth: +
No Growth: −
Control Culture: 8.00 × 10⁸ organisms per ml

| Ratio PD/MBT | .3 | .6 | 1.0 | 1.5 | 3.0 | 5.0 | 7.5 | 10 | 20 | 30 | 40 | 50 |
|---|---|---|---|---|---|---|---|---|---|---|---|---|
| 100/0* | + | + | + | + | + | + | + | + | + | + | + | + |
| 0/100 | + | + | + | + | + | + | − | − | − | − | − | − |
| 90/10 | + | + | + | + | + | + | + | + | − | − | − | − |
| 10/90 | + | + | + | + | − | − | − | − | − | − | − | − |
| 75/25 | + | + | + | + | + | + | + | + | − | − | − | − |
| 25/75 | + | + | + | + | − | − | − | − | − | − | − | − |
| 50/50 | + | + | + | + | − | − | − | − | − | − | − | − |

| Ratio PD/MBT | $\frac{Q_a + Q_b}{Q_A + Q_B}$ | Rating |
|---|---|---|
| 90/10 | 0.285 | <1 Synergy |
| 10/90 | 0.360 | <1 Synergy |
| 75/25 | 0.682 | <1 Synergy |
| 25/75 | 0.301 | <1 Synergy |
| 50/50 | 0.202 | <1 Synergy |

Calculations

TABLE I-continued
SYNERGISM STUDY FOR COMBINATION BIOCIDES AGAINST BACTERIA $Q_A$ = 1000 ppm active PD  
$Q_B$ = 7.5 ppm active MBT  
$\frac{Q_a}{Q_A} + \frac{Q_b}{Q_B} < 1$ = Synergy A. 90/10  
   $Q_a$ = 20 ppm × .90 = 18  
   $Q_b$ = 20 ppm × .10 = 2

$\frac{18}{1000} + \frac{2}{7.5} = 0.285$

B. 10/90  
   $Q_a$ = 3 ppm × .10 = .3  
   $Q_b$ = 3 ppm × .90 = 2.7

$\frac{.3}{1000} + \frac{2.7}{7.5} = 0.360$

C. 75/25  
   $Q_a$ = 20 ppm × 0.75 = 15  
   $Q_b$ = 20 ppm × 0.25 = 5

$\frac{15}{1000} + \frac{5}{7.5} = 0.682$

D. 25/75  
   $Q_a$ = 3 ppm × 0.25 = .75  
   $Q_b$ = 3 ppm × 0.75 = 2.25

$\frac{.75}{1000} + \frac{2.25}{7.5} = 0.301$

E. 50/50  
   $Q_a$ = 3 ppm × 0.50 = 1.5  
   $Q_b$ = 3 ppm × 0.50 = 1.5

$\frac{1.5}{1000} + \frac{1.5}{7.5} = 0.202$

*The end point of 1,5-pentanediol is 1000 ppm: 900 ppm showed growth; 1000 ppm showed no growth.

The combination of the methylene bis thiocyanate and 1,5-pentanedial is effectively used in treating pulp and papermill systems to prevent the growth and propagation of bacteria thereon. It is also useful in treating industrial cooling waters and injection waters used in the secondary and tertiary recovery flooding operations used to recover petroleum from underground formations.

Having thus described our invention, it is claimed as follows:

1. A synergistic biocidal composition useful in treating industrial process waters to prevent the growth of *Psuedomonas aeruginosa* which comprises the biocides 1,5-pentanedial and methylene bis thiocyanate in the following synergistic ratios and dosage ranges:

Ratio 1,5-Pentanedial/Methylene Bis Thiocyanate

90/10 at a dosage ranging between 20 ppm and 50 ppm,

10/90 at a dosage ranging between 3 ppm and 50 ppm,

75/25 at a dosage ranging between 20 ppm and 50 ppm,

25/75 at a dosage ranging between 3 ppm and 50 ppm,

50/50 at a dosage ranging between 3 ppm and 50 ppm.

* * * * *